United States Patent
Chen et al.

(10) Patent No.: US 7,768,260 B2
(45) Date of Patent: Aug. 3, 2010

(54) METHODS FOR IDENTIFICATION AND QUANTIFICATION OF MULTICOMPONENT-FLUID AND ESTIMATING FLUID GAS/ OIL RATIO FROM NMR LOGS

(75) Inventors: Songhua Chen, Katy, TX (US); Jiansheng Chen, Houston, TX (US); Hyung T. Kwak, Spring, TX (US)

(73) Assignee: Baker Hughes Incorporated, Houston, TX (US)

( * ) Notice: Subject to any disclaimer, the term of this patent is extended or adjusted under 35 U.S.C. 154(b) by 363 days.

(21) Appl. No.: 11/678,341

(22) Filed: Feb. 23, 2007

(65) Prior Publication Data
US 2008/0206887 A1   Aug. 28, 2008

(51) Int. Cl.
G01V 3/00 (2006.01)
(52) U.S. Cl. .................. 324/303; 324/306; 324/307
(58) Field of Classification Search ......... 324/300–322;
600/410, 411, 419–421; 436/173; 585/639,
585/640; 208/251 R; 525/240, 191; 524/543;
623/36; 424/401
See application file for complete search history.

(56) References Cited

U.S. PATENT DOCUMENTS

| | | | | |
|---|---|---|---|---|
| 3,087,888 | A * | 4/1963 | Saraceno | 208/251 R |
| 4,710,713 | A | 12/1987 | Strikman | |
| 5,712,566 | A | 1/1998 | Taicher et al. | |
| 6,229,308 | B1 * | 5/2001 | Freedman | 324/303 |
| 6,859,032 | B2 | 2/2005 | Heaton et al. | |
| 6,859,033 | B2 * | 2/2005 | Speier | 324/303 |
| 6,891,369 | B2 * | 5/2005 | Hurlimann et al. | 324/303 |
| 7,226,484 | B2 * | 6/2007 | Chen | 623/36 |
| 7,372,264 | B2 * | 5/2008 | Akkurt et al. | 324/303 |
| 7,396,971 | B2 * | 7/2008 | Smith et al. | 585/640 |
| 7,629,416 | B2 * | 12/2009 | Li et al. | 525/191 |
| 2003/0016013 | A1 * | 1/2003 | Kruspe et al. | 324/303 |
| 2003/0128032 | A1 * | 7/2003 | Heaton et al. | 324/303 |
| 2003/0178994 | A1 * | 9/2003 | Hurlimann et al. | 324/303 |
| 2004/0024276 | A1 * | 2/2004 | Smith et al. | 585/639 |
| 2004/0041562 | A1 * | 3/2004 | Speier | 324/303 |
| 2005/0008669 | A1 * | 1/2005 | Chen | 424/401 |
| 2005/0216196 | A1 | 9/2005 | Akkurt et al. | |
| 2006/0173123 | A1 * | 8/2006 | Yang et al. | 524/543 |
| 2006/0250130 | A1 * | 11/2006 | Akkurt et al. | 324/303 |
| 2008/0206887 | A1 * | 8/2008 | Chen et al. | 436/173 |
| 2008/0227919 | A9 * | 9/2008 | Li et al. | 525/240 |

OTHER PUBLICATIONS

Hirasaki, et al. "NMR properties of petroleum reservoir fluids". Magnetic Resonance Imaging 21 (2003) 269-277.

(Continued)

*Primary Examiner*—Brij B. Shrivastav
*Assistant Examiner*—Tiffany A Fetzner
(74) *Attorney, Agent, or Firm*—Cantor Colburn LLP

(57) ABSTRACT

A method for determining a proportion of a hydrocarbon constituent in a mixture including at least one hydrocarbon, includes determining at least one nuclear magnetic resonance (NMR) property for at least one hydrocarbon constituent in the mixture; correlating an NMR response for the property for each hydrocarbon constituent in the mixture; and from the correlating, calculating the proportion of at least the constituent. A computer program product is also provided.

20 Claims, 10 Drawing Sheets

OTHER PUBLICATIONS

International Search Report for International Application No. PCT/US20081054232. Mailed Dec. 9, 2008.

Written Opinion of the International Searching Authority for International Application No. PCT/US2008/054232. Mailed Dec. 9, 2008.

Chen et al., Estimation of Hydrocarboon Viscosity with multiple TE Dual Wait-Time MRIL Logs, Society of Petroleum Engineers, SPE 49009, 1998, pp. 1-14.

Chen et al., Improving the Accuracy of NMR Relaxation Distribution Analysis in Clay-Rich Reservoirs and Core Samples, paper SCA 9702, in 1997 international symposium proceedings: Society of Professional Well Log Analysts, Society of Core Analysts Chapter-at-large, p. 10, 1997.

Zhang, G.J., Wang, G.L., and Wang, H.M, 1999, "Application of novel basis functions in a hybrid method simulation of the response of induction logging in axisymmetrical stratified media," Radio Science, v. 34, No. 1, pp. 19-26.

Stegemeier, G.L. and H.J. Vinegar. 1995. "Soil Remediation by Surface Heating and Vacuum. Extraction," paper SPE 29771. pp. 781-797.

Freedman, R. et al., "A New NMR Method of Fluid Characterization in Reservoir Rocks: Experimental Confirmation and Simulation Results", Copyright Dec. 2001, Society of Petroleum Engineers Journal, pp. 452-464.

Lo, Sho-Wei, et al., "Mixing Rules and Correlations of NMR Relaxation Time with Viscosity, Diffusivity, and Gas/Oil Ratio of Methane/Hydrocarbon Mixtures", Copyright March 2002, Society of Petroleum Engineers Journal, pp. 24-34.

\* cited by examiner

-- PRIOR ART --

-- PRIOR ART --

-- PRIOR ART --

-- PRIOR ART --

-- PRIOR ART --

Dry gas interval
$T_1/T_{2app} > 100$ high GOR interval
$T_1/T_{2app} \sim 15$

US 7,768,260 B2

METHODS FOR IDENTIFICATION AND QUANTIFICATION OF MULTICOMPONENT-FLUID AND ESTIMATING FLUID GAS/ OIL RATIO FROM NMR LOGS

BACKGROUND OF THE INVENTION

1. Field of the Invention

The teachings herein provide techniques for determining properties of various hydrocarbon constituents in a mixture, wherein the mixture is surveyed using a nuclear magnetic resonance (NMR) instrument.

2. Description of the Related Art

A downhole fluid characterization method, such as one implemented by the Reservoir Characterization Instrument (RCI) (produced by Baker Hughes, Incorporated of Houston, Tex.) is used to determine light hydrocarbon types in a formation. This is completed by measuring pressure gradients in a reservoir section. Such measurements treat the fluid as a bulk fluid despite the fact that the fluid may contain multiple components. For example, the fluid may include mixtures of hydrocarbons or mixtures of hydrocarbons and non-hydrocarbon fluids. Thus, classification of hydrocarbon mixtures, such as those having a high gas-to-oil-ratio (GOR) or a low GOR as well as gas condensates can only be inferred qualitatively.

The most commonly inferred parameters for characterizing crude oil in the petroleum industry is either viscosity or fluid density. Both parameters are bulk fluid properties that do not provide for discrimination of compositions of the underlying fluids. In other words, from a measured viscosity or density value alone, one does not have sufficient information to determine whether the fluid generally includes only one type of hydrocarbon molecule, or a mixture of more than one type of hydrocarbon molecules.

On the other hand, use of NMR provides for molecular level characterization of a fluid. That is, NMR may be used to determine information regarding molecular-level interactions among the various molecules. Therefore, a bulk fluid having a hydrocarbon of a single molecular type may have a different NMR response than another bulk fluid that is a mixture having multiple types of hydrocarbon molecules. This is the case even where viscosity, $\eta$, of the two bulk fluids is similar or identical. Other techniques for performing microscopic analyses are known. However, these have certain limitations.

For example, although optical technology can in principle provide information regarding individual fluid components in hydrocarbon mixtures, use of optical technology has limitations when optical response of the various mixture components overlap.

Lo et al have studied various aspects of mixtures of hydrocarbons. The mixtures formed are primarily binary (i.e., the mixtures include a first molecule of interest and a second molecule of interest). The studies of Lo et al. have considered gas and oil mixtures as well as oil and oil mixtures. The studies provide that NMR relaxation time or diffusivity distributions from the mixtures may exhibit bimodal distribution patterns. The patterns depend on how close respective relaxation times or diffusivities are, as well as the relative amounts of the individual components in the mixtures.

Other work has been done in this area. For example, in order to correlate NMR response arising from mixtures of hydrocarbon molecules to the commonly used viscosity estimate, Freedman et al introduced a concept of a constituent viscosity model (SPE Journal, December 2001, pp. 452-464, U.S. Pat. No. 6,859,032). Lo et al. have also a mixing rule for NMR based diffusivity and relaxation times in hydrocarbon mixtures (SPEJ, March 2002, pp. 24-34).

Therefore, what is needed is a technique for estimating properties of hydrocarbons in mixtures. Preferably, the technique provides for use of multiple NMR responses to provide the estimating for a variety of mixtures.

BRIEF SUMMARY OF THE INVENTION

Disclosed is a method for determining a proportion of a hydrocarbon constituent in a mixture including at least one hydrocarbon, by determining at least one nuclear magnetic resonance (NMR) property for at least one hydrocarbon constituent in the mixture; correlating an NMR response for the property for each hydrocarbon constituent in the mixture; and from the correlating, calculating the proportion of at least the constituent.

Also disclosed is a computer program product including machine readable instructions stored on machine readable media, the instructions for determining a proportion of a hydrocarbon constituent in a mixture including at least one hydrocarbon, by implementing a method that calls for determining at least one nuclear magnetic resonance (NMR) property for at least one hydrocarbon constituent in the mixture; correlating an NMR response for the property for each hydrocarbon constituent in the mixture; and from the correlating, calculating the proportion of at least the constituent.

Also disclosed is an instrument for determining downhole a proportion of a hydrocarbon constituent in a mixture including at least one hydrocarbon, the instrument including a nuclear magnetic resonance (NMR) apparatus adapted for performing NMR evaluations downhole, and a processor coupled to the apparatus, the processor including a link to a computer program product including machine readable instructions stored on machine readable media, the instructions for determining the proportion by implementing a method including determining at least one nuclear magnetic resonance (NMR) property for at least one hydrocarbon constituent in the mixture correlating an NMR response for the property for each hydrocarbon constituent in the mixture; and from the correlating, calculating the proportion of at least the constituent.

BRIEF DESCRIPTION OF THE DRAWINGS

The subject matter which is regarded as the invention is particularly pointed out and distinctly claimed in the claims at the conclusion of the specification. The foregoing and other features and advantages of the invention are apparent from the following detailed description taken in conjunction with the accompanying drawings in which:

DETAILED DESCRIPTION OF THE INVENTION

The teachings herein take advantage of various unique nuclear magnetic resonance (NMR) properties of materials to provide for determination of gas-to-oil-ratios (GOR) in mixtures of gas, oil, oil based mud (OBM), oil based mud filtrate (OBMF) as well as other fluids. The determination of other ratios may also be provided for by applying the teachings herein.

For perspective, this disclosure provides a review of techniques for well logging using nuclear magnetic resonance (NMR) technology, some background on NMR measurements and analysis for volumes having multiple constituents as well as consideration for some of the complexities of downhole characterizations. A presentation of data and an evaluation of the data is provided. Aspects of information presented are then applied to disclose techniques for estimating GOR, viscosity, and performing some quantitative determinations. First, turn to FIG. 1 to consider aspects of downhole NMR characterizations, using a non-limiting embodiment of a wireline logging device. One skilled in the art will recognize that the techniques disclosed herein can be applied with other embodiments, such as logging-while-drilling (LWD) or measurements-while-drilling (MWD) operations.

Figure 1:
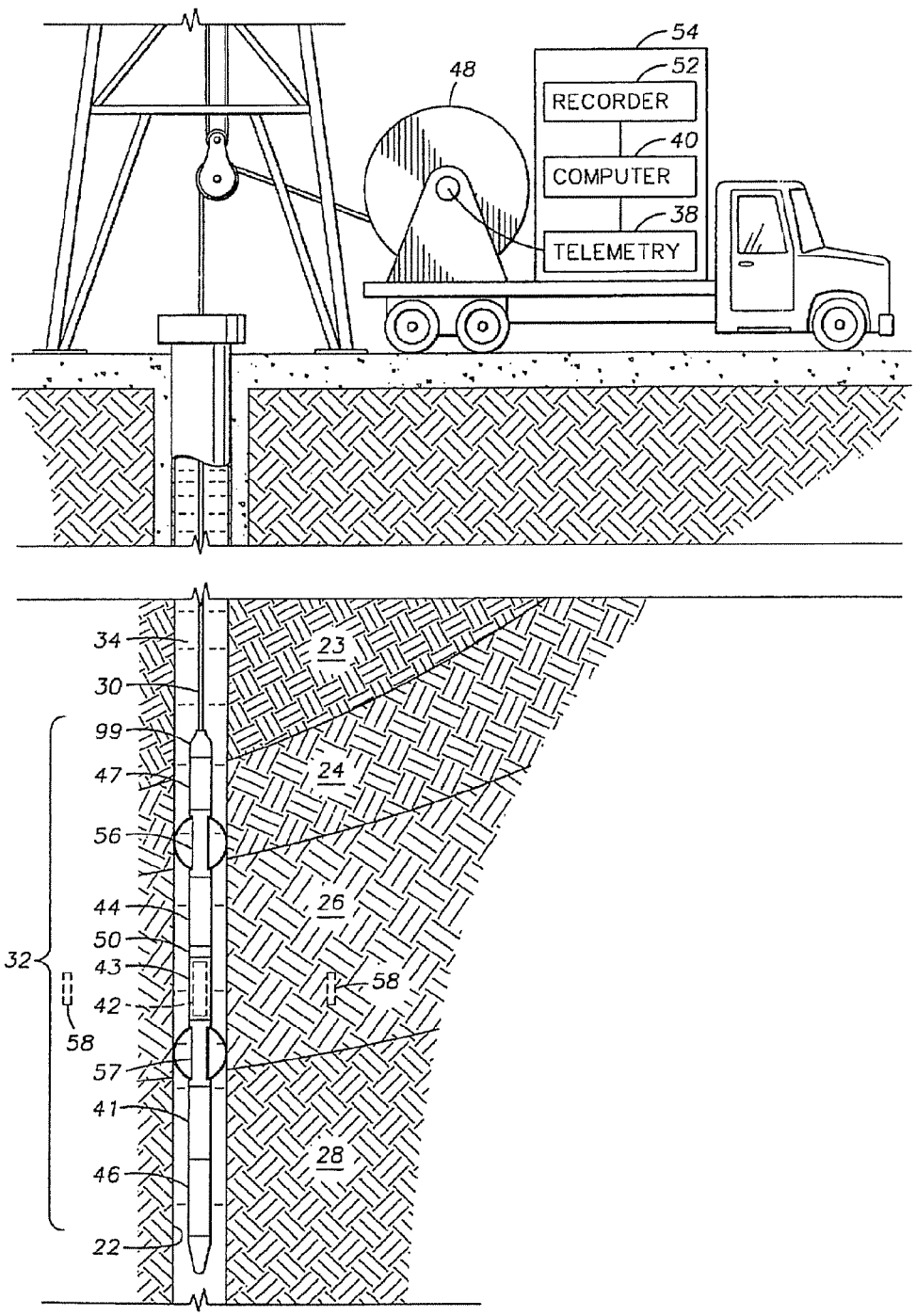
FIG. 1 depicts aspects of well logging with an nuclear magnetic resonance (NMR) apparatus.

FIG. 1 shows a well logging apparatus disposed in a wellbore 22 penetrating earth formations 23, 24, 26, 28 for making measurements of properties of the earth formations 23, 24, 26, 28 downhole. The wellbore 22 in FIG. 1 is typically filled with a fluid 34 known in the art as "drilling mud." A "sensitive volume," shown generally at 58 and having a generally cylindrical shape, is disposed in one of the earth formations, shown at 26. The sensitive volume 58 is a predetermined portion of the earth formations 26 in which nuclear magnetic resonance (NMR) measurements are made, as will be further explained.

In typical embodiments, the sensitive volume 58 includes materials such as would be found downhole (below the surface and within or around the wellbore 22) including a mixture of liquids including gas, water, drilling fluid, oil and formation fluids that are indigenous to the formations 23, 24, 26, 28.

A string of logging tools 32, which can include an NMR apparatus according to the present invention, is typically lowered into the wellbore 22 by, for example, an armored electrical cable 30. The cable 30 can be spooled and unspooled from a winch or drum 48. The tool string 32 can be electrically connected to surface equipment 54 by an insulated electrical conductor (not shown separately in FIG. 1) forming part of the cable 30. The surface equipment 54 can include one part of a telemetry system 38 for communicating control signals and data to the tool string 32 and computer 40. The computer may also include a data recorder 52 for recording measurements made by the apparatus and transmitted to the surface equipment 54. Typically, the computer includes a variety of input/output devices and other supporting devices to enhance the operation of the apparatus and estimations performed by use thereof. An NMR probe 42 can be included in the tool string 32.

Circuitry for operating the NMR probe 42 can be located within an NMR electronics cartridge 44. The circuitry can be connected to the NMR probe 42 through a connector 50. The NMR probe 42 is typically located within a protective housing 43 which is designed to exclude the drilling mud 34 from the interior of the probe 42. The function of the probe 42 will be farther explained.

Other well logging sensors (not shown separately for clarity of the illustration in FIG. 1) may form part of the tool string 32. As shown in FIG. 1, one additional logging sensor 47 may be located above the NMR electronics cartridge 44. Other logging sensors, such as shown at 41 and 46 may be located within or below the bottom centralizer 57. The other sensors 41, 46, 47 can be of types familiar to those skilled in the art.

Other aspects of the exemplary embodiment of the NMR probe 42 are provided in U.S. Pat. No. 5,712,566, entitled "Nuclear Magnetic Resonance Apparatus and Method," issued Jan. 27, 1998 to Taicher et al., and incorporated herein by reference in it's entirety. Another non-limiting example is disclosed in U.S. Pat. No. 4,710,713, also issued to Taicher et al, and also incorporated by reference herein in it's entirety. It should be recognized that these embodiments of NMR tools are exemplary only, and not limiting of the teachings herein. A commercially available and exemplary embodiment of an NMR instrument is the MREX™, available from Baker Hughes, Incorporated of Houston Tex.

One skilled in the art will recognize that while the teachings herein may be performed downhole, they are also applicable to evaluations conducted on the surface, such as in a laboratory. Further, and as discussed elsewhere herein, at least a portion of an evaluation or determination may be performed in one place or another. For example, a property of a constituent may be determined in a laboratory, while other measurements and determinations are performed downhole.

As a matter of convention, one should note that the variables used herein appear throughout the disclosure. Accordingly, previously defined variables are generally not reintroduced. For convenience of referencing, the following representations are some of the definitions applied herein, or related to the teachings herein: $B_0$ represents static field strength; $B_1$ represents radiofrequency (RF) field strength; D represents diffusivity; e,E represents echo amplitude with and without noise included; f represents a proton fraction; G represents RF field gradient strength; k represents a number of constituents (i.e., molecular types) within the mixture, and may be used as a subscript; M represents echo magnetization amplitude; where $M_z(t)$ represents a longitudinal magnetization, which involves a time constant $T_1$, where $T_1$ is the time required for the magnetization vector to be restored to 63% of its original amplitude (referred to as "longitudinal relaxation time"); $M_{x,y}$ represents a transverse magnetization, which involves a time constant $T_2$, where $T_2$ is the time required for the magnetization vector to drop to 37% of its original amplitude (referred to as "transverse relaxation time"); $T_{2B}$ represents a bulk fluid transverse relaxation time; $T_{2cutoff}$ represents a dividing time; $T_{2diff}$ represents the characteristic decay time due to molecular diffusion in a magnetic field gradient environment; $T_{1,2inter}$ represents transverse and longitudinal relaxation time due to intermolecular interactions; $T_{1,2intra}$ represents transverse and longitudinal relaxation time due to intramolecular interactions; $T_{2surf}$ represents a surface relaxation time; $T_E$ represents an inter-echo time; $T_W$ represents a wait time; and $t_k$ represents the time at the formation of the $k^{th}$ echo; v represent a frequency, and η represents viscosity.

Consider some of the aspects of performing NMR characterizations downhole. First, it should be noted that, as discussed herein, individual molecules generally do not experience chemical changes while in a mixture. Various techniques for characterization yield various results. That is, certain NMR techniques return separate results for different components, while others do not provide component specific information. In the exemplary embodiment, $T_2$ and D distributions may be observed for individual components (i.e., constituents of the mixture), or a broad, overlapping spectrum (depending on relative concentration of the molecules in the mixture).

Figure 2A:
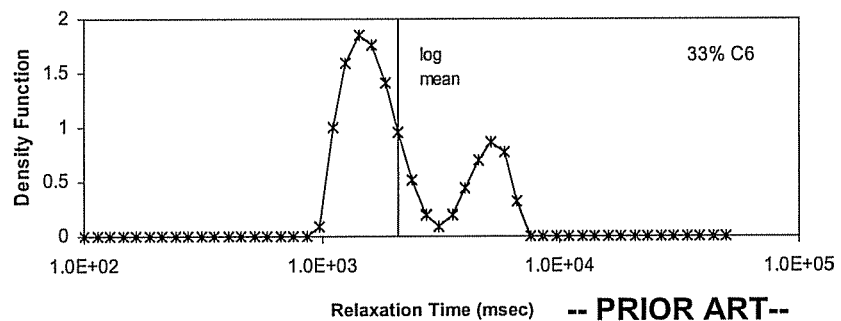
FIG. 2A, FIG. 2B and FIG. 2C, collectively referred to herein as FIG. 2, depict density functions for mixture of C6 and C16 hydrocarbons.
Figure 2B:
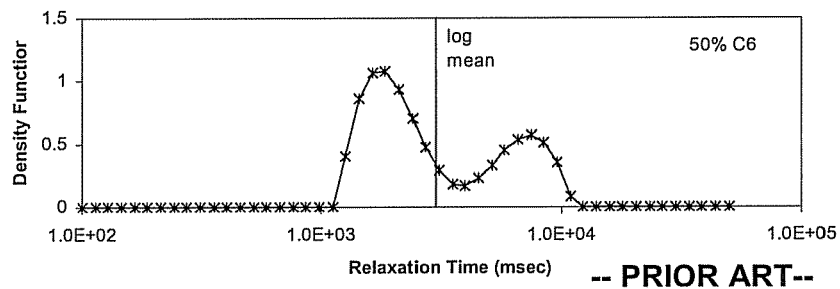
Figure 2C:
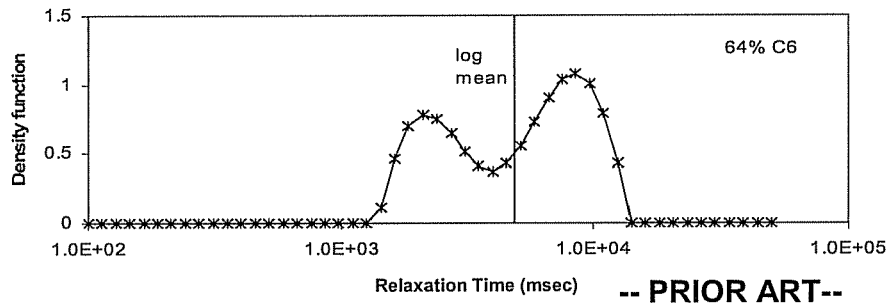
Figure 3A:
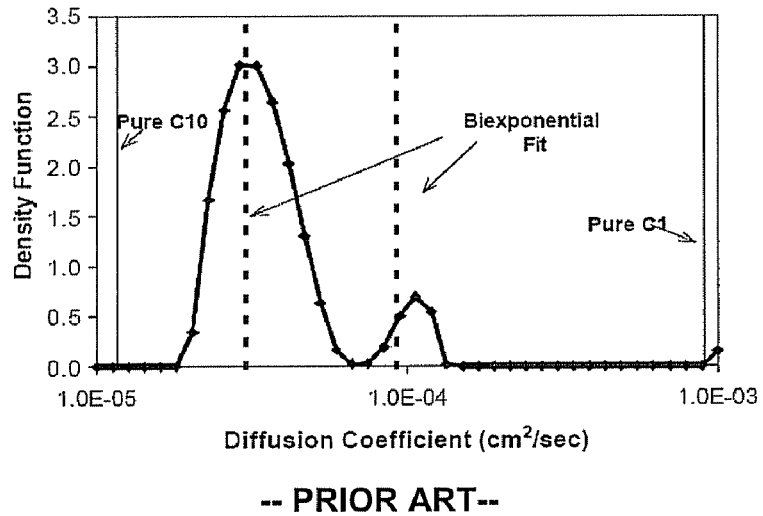
FIG. 3A and FIG. 3B, collectively referred to herein as FIG. 3, depict density functions for mixtures of hydrocarbons in comparison to predictions by various mixing rules.
Figure 3B:
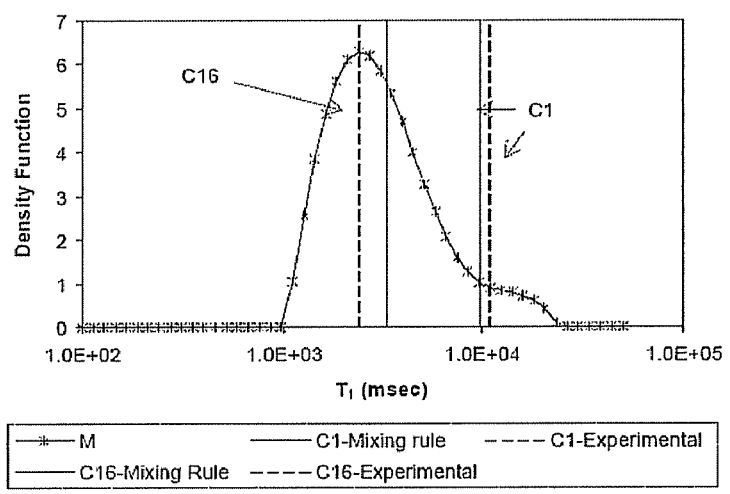

Typically, there are higher values for transverse relaxation time $T_2$ and diffusivity D for lighter hydrocarbon components. The relaxation time $T_2$ and diffusivity D for each component in a mixture shifts from a respective value in a non-mixture state and may become concentration dependent. Consider a mixture of C-6 and C-16 hydrocarbons. Transverse relaxation time $T_2$ data for the mixture are presented in Table 1. Similar data is provided in FIGS. 2 and 3. FIG. 3 also takes into consideration certain mixing rules.

TABLE 1

Mixture of C6 and C16 Oil

| C6 Wt. fraction | $T_2$ (C6) (secs) | $T_2$ (C16) (secs) | $T_2$ (log mean) |
|---|---|---|---|
| 0 | | 0.922 | 0.922 |
| 0.33 | 5.143 | 1.535 | 2.086 |
| 0.49 | 7.108 | 1.881 | 2.981 |
| 0.64 | 8.331 | 2.418 | 4.791 |
| 1 | 9.859 | | 9.859 |

For simplicity, the disclosure herein generally considers that the mixture is binary (i.e., the mixture includes two molecules of interest, molecule A and molecule B). It should be understood that the teachings herein may be applied to mixtures having more than two constituents or components (i.e., molecules of interest) in the mixture.

Figure 4:
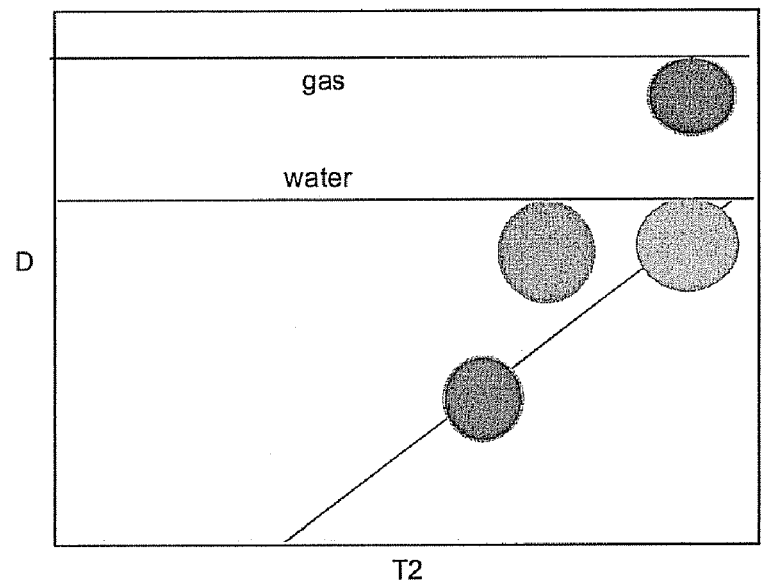
FIG. 4 depicts aspects of an exemplary two-dimensional analysis of NMR data.

Consider a wellbore 22 that has a high gas-to-oil ratio (GOR) and that has been drilled using oil based mud. Using a one-dimensional NMR analysis (i.e., considering the $T_2$ spectrum alone), native reservoir oil and oil based mud filtrate (OBMF) may be separable if they have substantially different viscosity, η. However, dissolved gas and light oil components may exhibit similar transverse relaxation time $T_2$ while having different diffusivity D. Accordingly, a two-dimensional NMR analysis (i.e., considering the $T_2$ spectrum and the diffusivity, D) may be used to further distinguish the components of the mixture. Reference may be had to FIG. 4.

As an introduction to the teachings herein, consider the two-dimensional display of NMR data provided in FIG. 4. This depiction shows that components may be separable by the transverse relaxation time $T_2$ if oil and OBMF have different viscosities, $\eta_{oil}$, $\eta_{OBMF}$. Dissolved gas may be observed as a peak separate from the oil as the diffusivity D of the solution gas and oil are different. In FIG. 4, there is also a possible left-shift of $T_2$ (and not D) for an oil peak due to mixed wetting.

Figure 5:
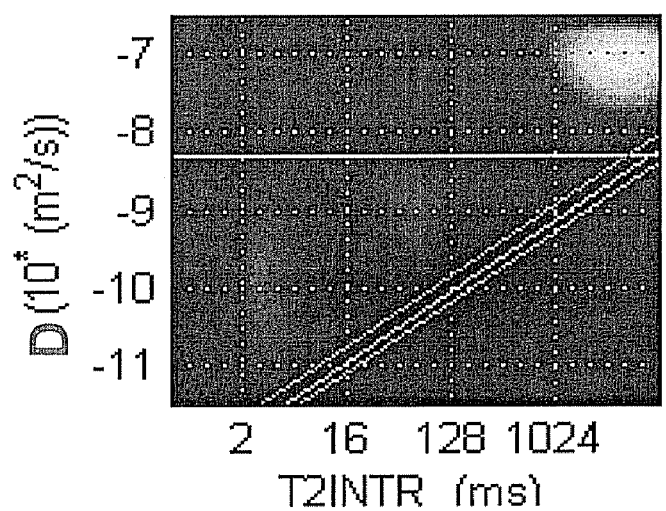
FIG. 5 through FIG. 7 depict two-dimensional analyses of NMR data for actual data.
Figure 6:
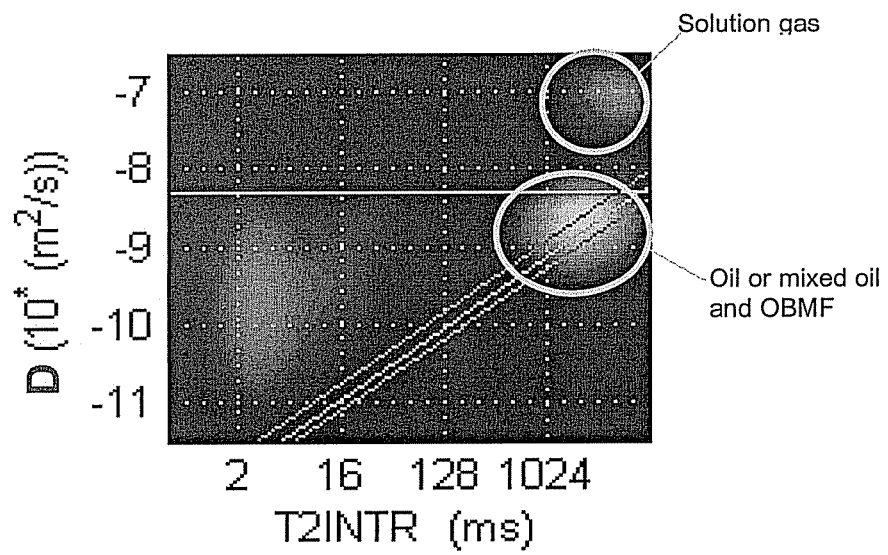
Figure 7:
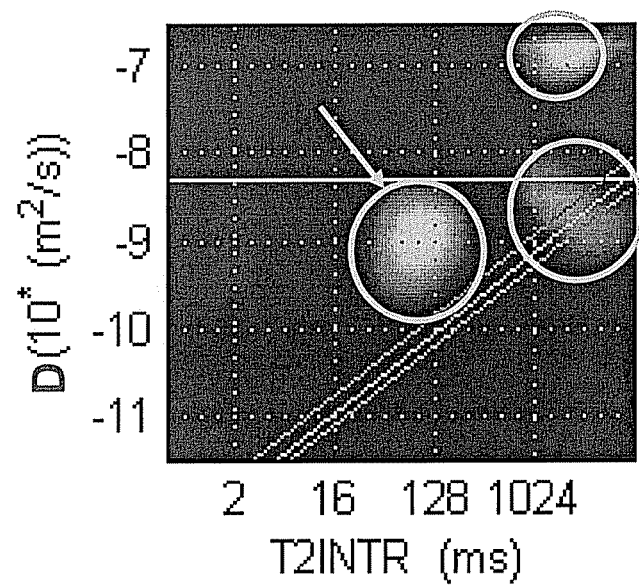

FIGS. 5-11 provide further depictions of NMR data. FIG. 5 shows a dry gas interval having a pronounced peak. There is no significant filtrate invasion identified in this gas interval. In FIG. 6, oil or mixed oil and oil based mud filtrate are also identified. FIG. 7 depicts a sample interval further including a potential mixture of mixed wettability (as denoted by the indicator arrow). This mixture has a reduced transverse relaxation time $T_2$ (but not diffusivity D). This can be problematic as mixed wetting can effect part of the oil signal. Although it is not probable, it is still possible that diffusivity of the oil is increased due to presence of dissolved gas.

Figure 8:
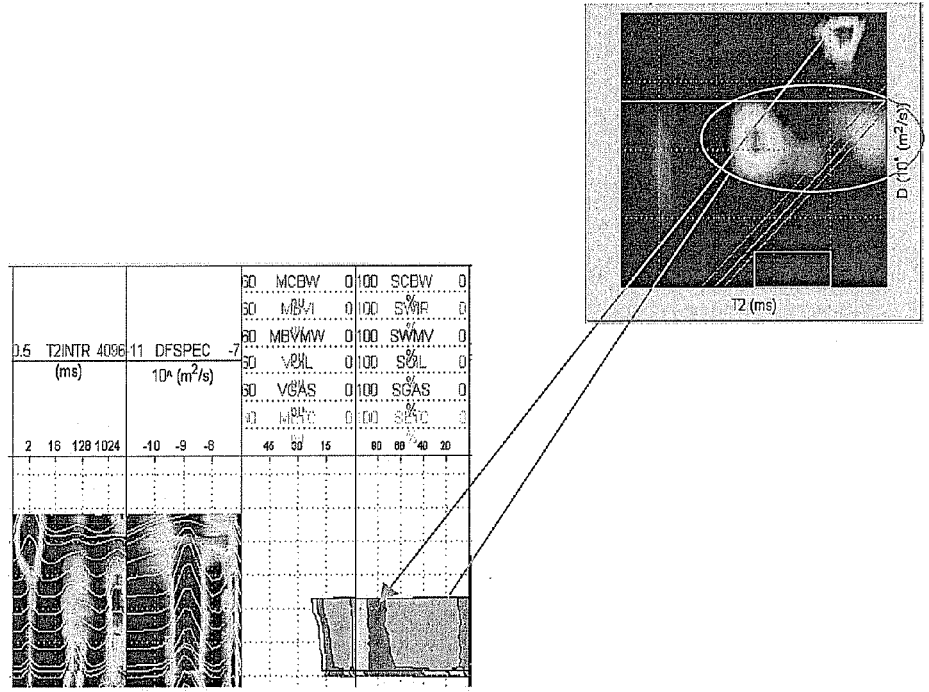
FIG. 8 depicts a correlation of a well log to a two-dimensional map.

FIG. 8 depicts aspects of a mixture of oil and OBMF (which is considered mixed wet OBMF). In this embodiment, theoretical analysis provides that for a given GOR, P and T, gas content is approximately 20% of the mixture. Applying experimental analysis, the gas content is approximately 25% of the mixture. This is consistent but semi-quantitative.

Figure 9A:
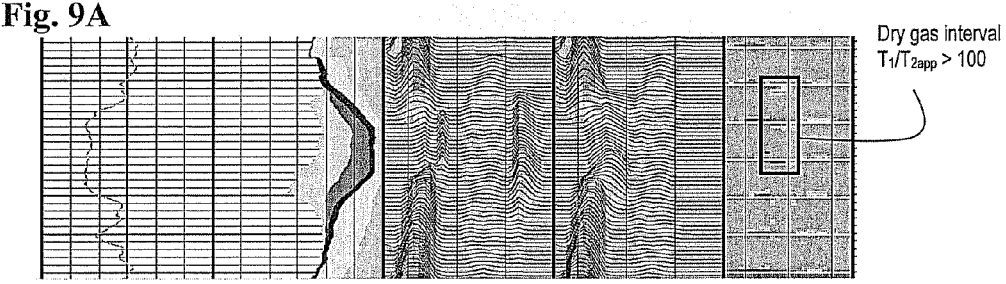
FIG. 9A and FIG. 9B, collectively referred to herein as FIG. 9, depict portions of well logs that correlate to maps of gas and high GOR zones.
Figure 9B:
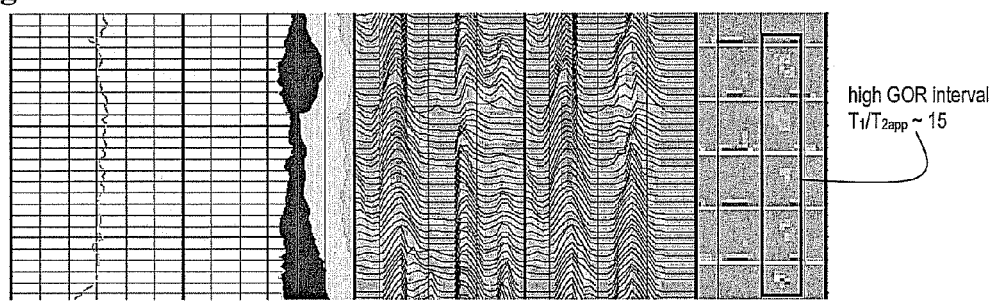
Figure 10A:
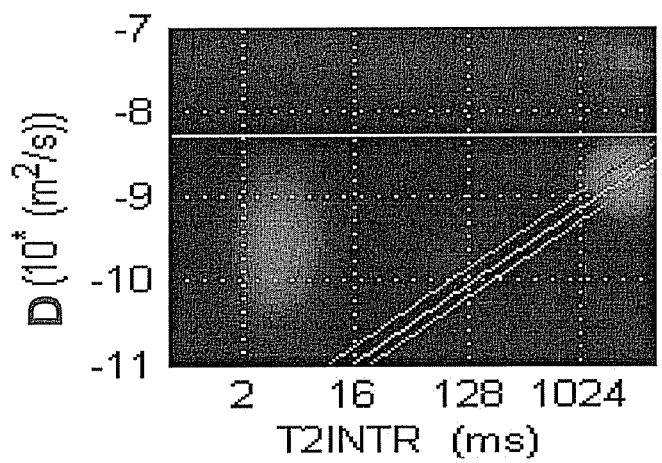
FIG. 10A, FIG. 10B and FIG. 10C, collectively referred to herein as FIG. 10, depict two dimensional maps that correlate to the well logs of FIG. 9.
Figure 10B:
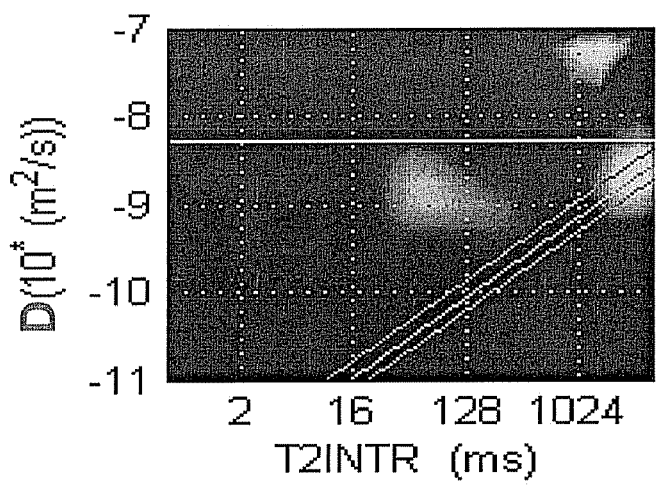
Figure 10C:
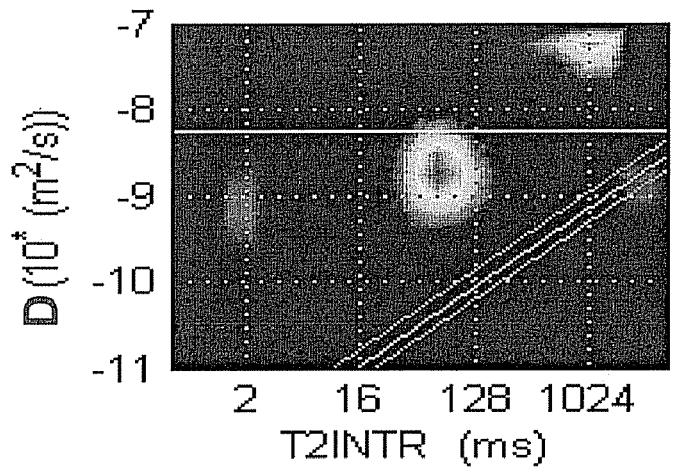

FIGS. 9A and 9B depict aspects of maps for gas and high GOR zones. In this example, $T_{2app}$ is computed from an inter-echo time $T_E$=1.4 ms, for a frequency v=686 kHz. Related two dimensional maps are provided in FIG. 10. In FIG. 10, the intensity of the individual two dimensional images were normalized to the highest intensity one among all of the two dimensional images.

Figure 11:
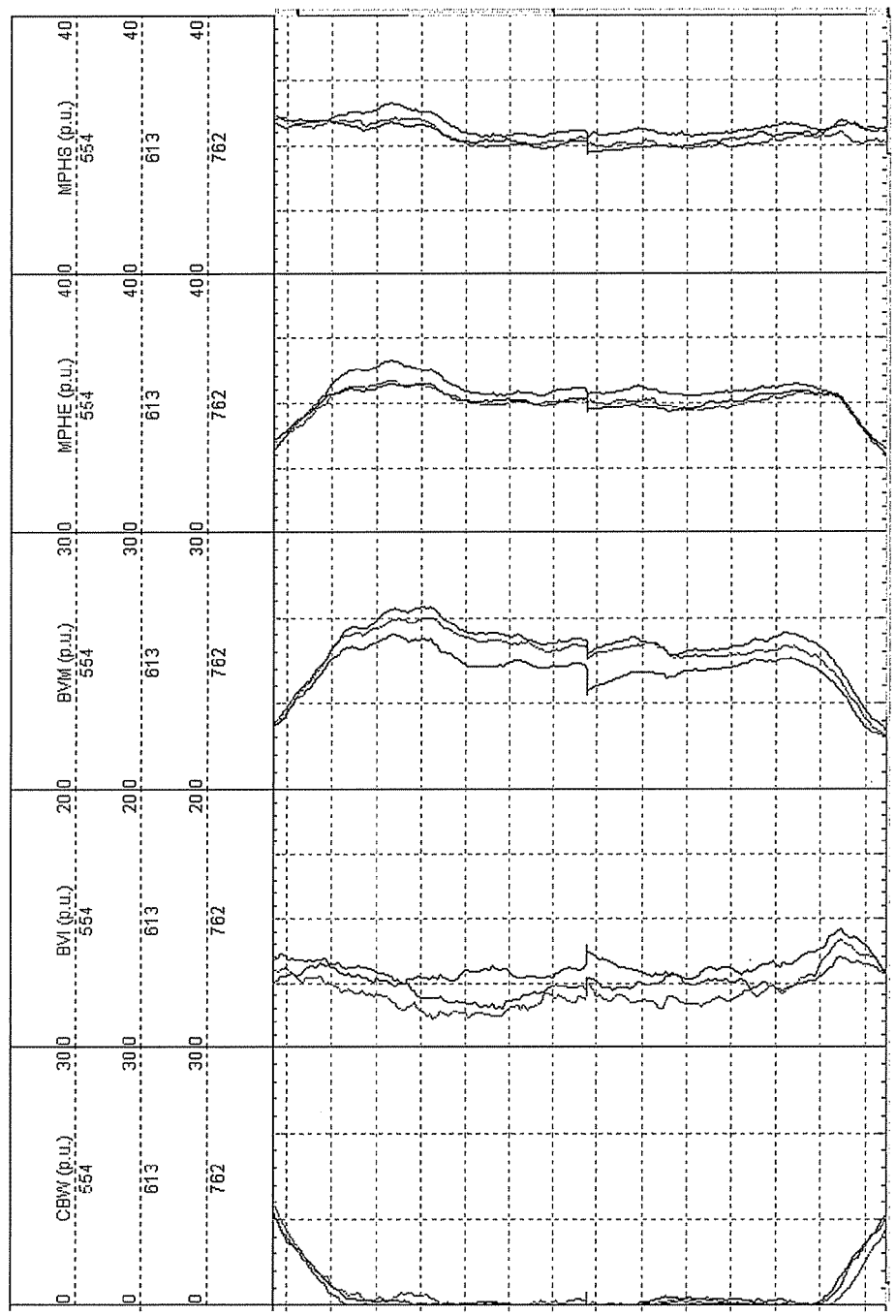
FIG. 11 depicts an exemplary well log for a system applying the teachings herein.

FIG. 11 depicts an exemplary well log for a system applying the teachings herein. In FIG. 11, no fine particle plugging was observed among the three DOIs (2.8, 3.4, 3.7 inches). The data involved a running average of thirty two data sets with individual frequency processing.

Mechanisms for NMR relaxation times of a fluid mixture can be generally described as due to intermolecular and intramolecular interactions, as given in Eq. (1):

$$\frac{1}{T_{1,2}} = \frac{1}{T_{1,2,intra}} + \frac{1}{T_{1,2,inter}}. \tag{1}$$

Spin-rotation is an intramolecular motion which dominates for small molecules such as gas molecules. The liquid hydrocarbon is often dominated by dipole-dipole interactions, which originate from either at least one of intramolecular and intermolecular interactions. The dipole-dipole interaction depends on the strength of the dipolar coupling (γ), on the orientation and distance between the interacting nuclei and on the motion.

$$\frac{1}{T_1^{DD}} = \frac{N\gamma_1^2\gamma_2^2\tau_c\hbar}{r_{12}^6}; \tag{2}$$

where $\gamma_1$ and $\gamma_2$ each represent a gyromagnetic ratio of nuclei involved in the interaction, $\tau_c$ represents a correlation time, $\hbar$ is Plank's constant, and $r_{12}$ represents distance between two nuclei.

Mixtures of hydrocarbons experience both the intermolecular and intramolecular interactions. Intermolecular interactions can be the results of the interaction between same or different hydrocarbon molecules. Thus, relaxation time for molecule A, $T_{1,2A}$, in a mixture of hydrocarbons (wherein the constituents k are principally molecule A and molecule B) is described by Eq. (3):

$$\frac{1}{T_{1,2A}} = \frac{1}{T_{1,2,intraA}} + \frac{\alpha}{T_{1,2,interA-A}} + \frac{\beta}{T_{1,2,interA-B}}; \tag{3}$$

where α and β are constitutive constants, and generally depend on concentration of the two molecules (A, B). Similarly, for molecule B of the mixture, Eq. (4) governs:

$$\frac{1}{T_{1,2B}} = \frac{1}{T_{1,2,intraB}} + \frac{\alpha}{T_{1,2,interB-B}} + \frac{\beta}{T_{1,2,interA-B}}. \quad (4)$$

As long as the terms $$\frac{1}{T_{1,2,intraA}} \text{ and } \frac{1}{T_{1,2,intraB}}$$

are sufficiently different from each other and are more significant than the intermolecular interaction terms, the two molecules relax at different rates. In this case, the relaxation rates $T_{1,2A}$, $T_{1,2B}$ are also different from the values measured for corresponding non-mixing states.

In cases where the two fluid molecules (A, B) are immiscible, the interaction between heterogeneous molecules (A-B) is considered generally small and a is approximately equal to one (1). Thus, the molecules A, B relax approximately at their corresponding relaxation times. However, this is not a case for immiscible phase fluids in a fine-emulsion state, such as where $\alpha < 1$.

Another relaxation mechanism in reservoir crude oil and gas is the paramagnetic relaxation because paramagnetic impurities often exist in reservoir fluids. The paramagnetic relaxation $T_1^{PM}$ caused relaxation rate enhancement by dipolar coupling to an electron spin and often can be expressed according to Eq. (5):

$$\frac{1}{T_1^{PM}} = \frac{4\pi^2 N_p \gamma^2 \mu_{eff}^2}{kT}; \quad (5)$$

where $N_p$ represents the number of paramagnetic ions present in the sensitive volume 58 and $\mu_{eff}$ represents the effective magnetic moment of the paramagnetic ion. Despite the complexity of relaxation time mechanisms especially for mixtures, in practice, it has been found that empirical mixing rules are useful for predicting NMR response and fluid properties.

Many mixing rules are known for predicting viscosity, $\eta$, of a hydrocarbon mixture from a relaxation time measurement. Knowledge of native oil viscosity, $\eta$, provides insight regarding reservoir simulation, reservoir quality assessment and is useful for predicting oil production. For an NMR based mixing rule, it has been predicted that individual hydrocarbon components having constituent viscosity, $\eta_k$, the viscosity $\eta$, may be determined according to Eq. (6):

$$\eta = \prod_k \eta_k^{f_k}; \quad (6)$$

while the log-mean relaxation time $T_{2,LM}$ for the aggregation of individual components (form their corresponding single component-alone state) may be determined according to Eq. (7):

$$T_{2LM} = \prod_k T_{2,k}^{f_k}; \quad (7)$$

where the $k_{th}$ component of hydrocarbon associates with relaxation time $T_{2,k}$ and having a proton fraction of $f_k$. It is noted that mixing rules are generally empirical.

Classification of mixtures using NMR response. Multiphase fluid systems encountered in NMR well logging generally include scenarios where: 1) both vapor and liquid phase hydrocarbons coexist; 2) oil based mud filtrate (OBMF) and native oils occupy different pores separately, such as may result from piston-type invasion flushing; 3) OBMF and native oils are well mixed in porous media; and 4) oil having a high gas-to-oil ratio (GOR) is encountered and contains solution gas mixed with other liquid hydrocarbon components or OBMF. Certain considerations apply to each situation.

As discussed herein "native oil" makes reference to deposits of hydrocarbons that are resident downhole and prior to penetration by the wellbore. Native oil typically includes a mixture of gas an oil. As one skilled in the art will understand, native oil deposits may experience invasion of OBMF during the drilling process, and mixing may occur in varying degrees.

For the first scenario, it is considered that gas and liquid phase hydrocarbons are separate and their relaxation times $T_{1,2}$ and diffusivity D should be sufficiently close to their respective vapor phase or liquid hydrocarbon phase relaxation times $T_{1,2}$. For the second scenario, it is considered that the relaxation time $T_{1,2B}$ of the two liquid hydrocarbon components together (i.e., OBMF and the native oils), should also be sufficiently close to the relaxation time $T_{1,2}$ for the fluids individually. Depending on how close the respective relaxation times $T_{1,2}$ are, a resultant relaxation time distribution of the fluids may exhibit bimodal or an overlapping unimodal appearance. For the third scenario, the relaxation time of the two liquid hydrocarbon components (i.e., OBMF and the native oils) depart from their respective, single-phase relaxation time $T_{1,2}$ values. The resultant relaxation time distribution of the mixed fluid may be unimodal or bimodal. The separation between the bimodal peaks may be smaller than that of the second scenario. In the fourth scenario, the hydrocarbon components in the mixture may also be non-unimodal. In other words, even though the hydrocarbon components appear macroscopically to be in a single fluid phase, NMR may provide information that reveals otherwise (such as at the molecular level).

For mixtures of fluids, such as those described in the above scenarios, present techniques yield a gross response for the entire mixture. The response is based on macroscopic fluid properties, such as a pressure-gradient based fluid density analysis or a viscosity measurement. Unfortunately, information about individual components is lost.

The invention disclosed herein provides for, among other things, identifying fluid properties for individual hydrocarbon constituents (i.e., components) in various forms of a mixture. As an example, first consider a technique for estimating the gas-to-oil ratio (GOR) in a situation where the mixture is described by the fourth ($4^{th}$) scenario.

In one embodiment, the high-GOR mixture (scenario 4), is described as having a fraction of protons from gas molecules $f_G$, a fraction of protons from liquid molecules $f_O$, and corresponding relaxation times denoted as $T_{2G}$ and $T_{2O}$ (in their respective gas-alone or oil-alone state). The viscosities of the separate constituent fluids (i.e., in a pure state) are denoted as $\eta_G$ and $\eta_O$, respectively. When the mixture (i.e., the high-GOR mixture) is measured, one obtains for the $T_2$ spectrum the gas and liquid components which have peak values of $T_{2g}$ and $T_{2o}$ (when evaluated in a mixture). Note that the mixture relaxation times $T_{2g}$ and $T_{2o}$ are somewhat different than the pure state relaxation times, $T_{2G}$ and $T_{2O}$ respectively. This may be seen with greater clarity with regard to the one-dimensional display in FIG. 8.

The teachings herein provide for solving for GOR from a measured bimodal relaxation time distribution having two peaks at $T_{2g}$ and $T_{2o}$. Although $T_{2g} \neq T_{2G}$ and $T_{2o} \neq T_{2O}$, the ratio of the areas under $T_{2g}$ and $T_{2o}$ (denoted as $f_g/f_o$) approximates $f_G/f_O$. Accordingly, an exemplary method for solving for GOR is provided in FIG. 9.

In the exemplary method for solving for GOR 30, a first step 31 calls for obtaining $T_2$ spectrum, a diffusivity D spectrum, or two-dimensional (2D) map ($T_2$ and diffusivity, D) and summarizing intensity under the two peaks ($T_{2g}$ and $T_{2o}$) separately. The result is denoted as $f_g$ and $f_o$, respectively. A second step 32 calls for computing the proton fraction ratio for gas and liquid components (denoted as $f_g/f_o$). A third step calls for converting the proton fraction ratio, $f_g/f_o$, to a gas and liquid volume ratio (GOR). Note that it is generally assumed that $T_{2g} \neq T_{2G}$ and $T_{2o} \neq T_{2O}$. Estimation of native oil viscosity, η, from an OBMF contaminated mixture is described by the third scenario above.

The third scenario describes a system where OBMF is well mixed with native oil and well disbursed within pores in the formations 23, 24, 26, 28.

The technique described in this embodiment provides for cases where the viscosities of the OBMF and native oil has substantially different; that is, where these two fluids include hydrocarbon molecules that are substantially different in carbon numbers such that the corresponding $T_2$ values are sufficiently different. In this embodiment, the relaxation time of the OBMF alone, $T_{2,OBMF}$, is known. The relaxation time of the OBMF alone, $T_{2,OBMF}$, is often readily available by prior knowledge, or by measuring the properties of the OBMF in a laboratory. The usually unknown relaxation time of the native oil, $T_{2O}$, is needed for estimating the native, reservoir oil viscosity. The log derived relaxation times shows two peaks at $T_{2,obmf}$ and $T_{2o}$ respectively, and in general, it may be considered that $T_{2,obmf} \neq T_{2,OBMF}$ and $T_{2o} \neq T_{2O}$.

In the present art, it is assumed that the log mean of $T_{2,OBMF}$ and $T_{2O}$, $T_{2LM} = T_{2OBMF}^{f_{OBMF}} \cdot T_{2O}^{f_o}$, is substantially close to the log mean of the measured relaxation time spectrum, $$T'_{2LM} = \prod_i T_{2i}^{f_i},$$

where $f_i$ is the individual bin-porosity corresponding to $T_{2i}$. It is also assumed that the OBMF and oil are separable on the $T_2$ spectrum such that $f_{OBMF} \lambda f_{obmf}$. In this case, the relaxation time for the native oil $T_{2O}$ may be computed (when the OBMF relaxation time $T_{2,OBMF}$) according to Eq. (8):

$$T_{2O} = \left( \frac{T'_{2LM}}{T_{2OBMF}^{f_{obmf}}} \right)^{1/f_o}; \quad (8)$$

Finally, by applying oil relaxation time to viscosity correlations, as are known in the art, one can estimate the native oil viscosity, η, from the relaxation time for the native oil $T_{2O}$. Reference may be had to FIG. 10.

For oil having a high GOR, the viscosity of the oil without dissolved gas, $η_o$, as well as the GOR can be farther used to estimate viscosity of live oil (i.e., oil downhole having a combination of gas an oil as constituents) using, for example, the empirical formula provided in Eq. (9):

$$η_{live} = a η_o^b \quad (9);$$

where $$a = 10.715 \cdot (GOR+100)^{-0.515} \quad (10);$$

$$b = 5.44 \cdot (GOR+150)^{-0.338} \quad (11).$$

Similarities between these embodiments (involving mixtures of native oil and oil based mud filtrate) and embodiments involving mixtures of gas and oil are present. Consider the graph presented in FIG. 11 depicting exemplary relaxation times.

In further embodiments, the teachings provide for estimating the quantity of OBMF and native oil when measurement data overlaps. In this embodiment, another aspect of the third scenario is considered. In this instance, both the OBMF and native oil viscosities, η, are known. However, NMR response signals for the native oil and OBMF are considerably overlapped ($T_2$ and/or diffusivity D). Accordingly, the objective is to determine quantities of native hydrocarbon and the OBMF. An exemplary method for this is provided in FIG. 12.

Figure 12:
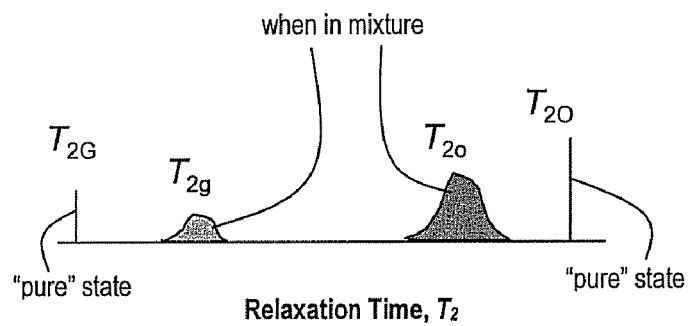
FIG. 12 depicts an exemplary one-dimensional map for relaxation time, $T_2$.
Figure 13:
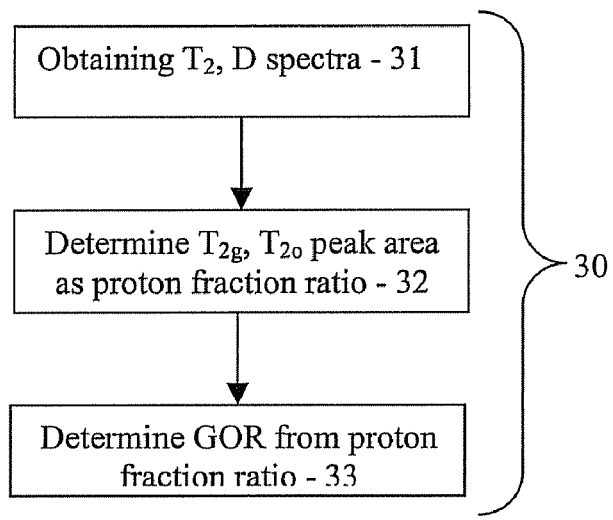
FIG. 13 depicts an exemplary method.
Figure 14:
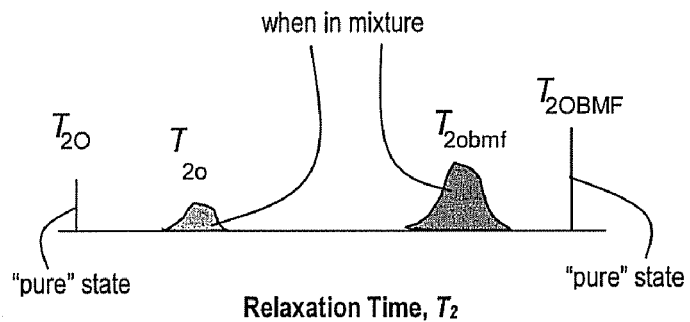
FIG. 14 depicts another exemplary one-dimensional map for relaxation time, $T_2$.
Figure 15:
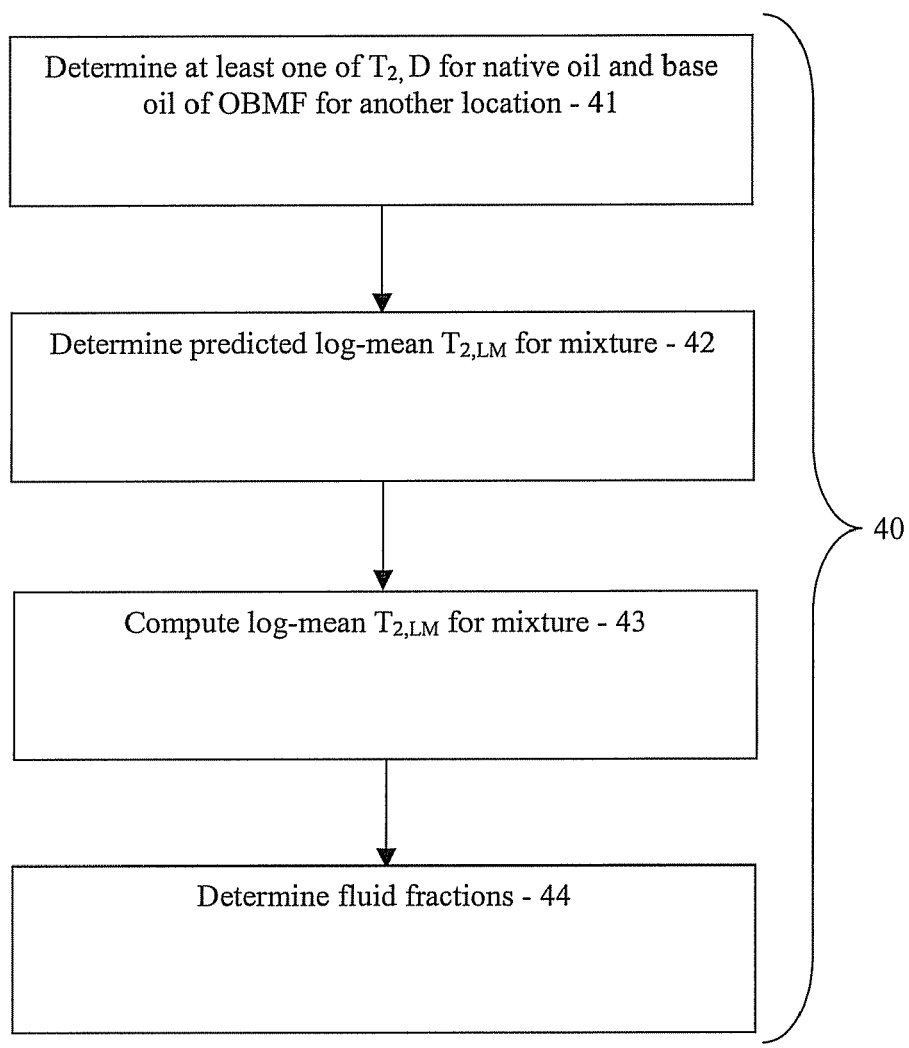
FIG. 15 depicts another exemplary method.

In FIG. 12, the exemplary method 40 for determining quantities of native hydrocarbon and OBMF when NMR measurements overlap generally calls for four steps. In a first step 41, the native oil and base oil of the OBMF from the same reservoir for an adjacent well is determined. Typically, this calls for measuring the NMR response (such as $T_2$ and diffusivity) directly, or learning the property such as by deriving the NMR response using known correlations or referring to a source of property information. In a second step 42, the predicted log-mean $T_2$ response of the mixture fluid is formulated, assuming an appropriate mixing rule is known. The fraction of invaded OBMF is unknown. Eq. (12) provides an exemplary formulation for predicting the log-mean $T'_{2LM}$ response.

$$\log T'_{2LM} = f_{OBMF} \cdot \log T_{2OBMF} + (1 - f_{OBMF}) \cdot \log T_O \quad (12);$$

In a third step 43, the log-mean of the mixture $T_{2,LM}$ is computed from the $T_2$ distribution. In a fourth step 44, the OBMF fluid fraction $f_{OBMF}$ with the measured $T_{2LM}'$ is computed. This may be computed according to Eq. (13):

$$f_{OBMF} = \log \frac{T'_{2LM}}{T_{2O}} \Big/ \log \frac{T_{2OBMF}}{T_{2O}}; \quad (13)$$

In the fourth step 44, the native oil fraction is determined from the OBMF fluid fraction $f_{OBMF}$. This is computed according to Eq. (14):

$$f_O = 1 - f_{OBMF}. \quad (14);$$

In this exemplary method 40, the technique involves only the transverse relaxation time $T_2$. However, one skilled in the art will recognize that the technique can be applied to longitudinal relaxation time $T_1$, diffusivity D, and the cross-plot of the two (commonly known as two-dimensional (2D) NMR) as well as cross-plots between diffusivity D and $T_2$, between $T_1$ and $T_2$, and the combinations thereof.

In support of the teachings herein, various analysis components may be used, including digital and/or an analog systems. The system may have components such as a computer, a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a sample line, sample storage, sample chamber, sample exhaust, pump, piston, power supply (e.g., at least one of a generator, a remote supply and a battery), vacuum supply, pressure supply, refrigeration (i.e., cooling) unit or supply, heating component, motive force (such as a translational force, propulsional force or a rotational force), magnet, electromagnet, sensor, electrode, transmitter, receiver, transceiver, controller, optical unit, electrical unit or electromechanical unit may be included in support of the various aspects discussed herein or in support of other functions beyond this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for determining a proportion of a hydrocarbon constituent in a mixture comprising at least one hydrocarbon, the method comprising:

determining at least one nuclear magnetic resonance (NMR) property for at least one hydrocarbon constituent in the mixture;

correlating an NMR response for the property for each hydrocarbon constituent in the mixture; and from the correlating, calculating the proportion of at least the constituent, wherein calculating includes calculating a gas-to-oil ratio (GOR) for the mixture, wherein calculating the GOR includes:

determining a transverse relaxation time ($T_2$) spectrum for the mixture;

calculating a proton fraction ratio of gas molecules to liquid molecules from the $T_2$ spectrum; and converting the proton fraction to the GOR for the mixture.

2. The method as in claim 1, wherein the determining a proportion comprises performing the determining in at least one of downhole and in a laboratory.

3. The method as in claim 1, wherein the property comprises at least one of a longitudinal relaxation time $T_1$, a transverse relaxation time $T_2$, and a diffusivity, D.

4. The method as in claim 1, wherein the determining at least one NMR property comprises measuring the property for the constituent when the constituent is separate from the mixture.

5. The method as in claim 1, wherein the determining comprises learning the property by at least one of deriving the property and referring to a source of information.

6. The method as in claim 1, wherein the determining comprises predicting a log-mean value for the property of the at least one hydrocarbon.

7. The method as in claim 6, further comprising applying a mixing rule to determine the log-mean value.

8. The method as in claim 1, further comprising using the NMR response to determine viscosity of a constituent and a viscosity of live oil.

9. The method as in claim 1, further comprising obtaining an NMR response for each property for the at least one constituent.

10. The method as in claim 1, wherein the NMR response comprises a proton fraction ratio for each of the constituents.

11. The method as in claim 1, wherein the correlating comprises producing a two-dimensional map of the property.

12. An instrument for determining downhole a proportion of a hydrocarbon constituent in a mixture comprising at least one hydrocarbon, the instrument comprising:

a nuclear magnetic resonance (NMR) apparatus adapted for performing NMR evaluations downhole, and a processor coupled to the apparatus, the processor comprising a link to a computer program product comprising machine readable instructions stored on machine readable media, the instructions for determining the proportion, by implementing a method comprising:

determining at least one nuclear magnetic resonance (NMR) property for at least one hydrocarbon constituent in the mixture;

correlating an NMR response for the property for each hydrocarbon constituent in the mixture; and from the correlating, calculating the proportion of at least the constituent, wherein calculating includes calculating a gas-to-oil ratio (GOR) for the mixture, wherein calculating the GOR includes:

determining a transverse relaxation time ($T_2$) spectrum for the mixture;

calculating a proton fraction ratio of gas molecules to liquid molecules from the $T_2$ spectrum; and converting the proton fraction to the GOR for the mixture.

13. A computer program product comprising machine readable instructions stored on machine readable media, the instructions for determining a proportion of a hydrocarbon constituent in a mixture comprising at least one hydrocarbon, by implementing a method comprising:

determining at least one nuclear magnetic resonance (NMR) property for at least one hydrocarbon constituent in the mixture;

correlating an NMR response for the property for each hydrocarbon constituent in the mixture; and from the correlating, calculating the proportion of at least the constituent, wherein calculating includes calculating a gas-to-oil ratio (GOR) for the mixture, wherein calculating the GOR includes:
- determining a transverse relaxation time ($T_2$) spectrum for the mixture;
- calculating a proton fraction ratio of gas molecules to liquid molecules from the $T_2$ spectrum; and
- converting the proton fraction to the GOR for the mixture.

14. The computer program product as in claim 13, wherein the property comprises obtaining at least one of a longitudinal relaxation time $T_1$ spectrum, a transverse relaxation time $T_2$ spectrum, a diffusivity D spectrum.

15. The computer program product as in claim 13, wherein the correlating comprises associating an intensity for the NMR response with a proton fraction for each constituent.

16. The computer program product as in claim 13, wherein the calculating comprises converting a proton fraction ratio to a volume ratio.

17. The computer program product as in claim 13, wherein the mixture comprises oil based mud filtrate (OBMF) and oil (O).

18. The computer program product as in claim 17, wherein the correlating comprises formulating a predicted log-mean response transverse relaxation time, $\log T'_{2LM}$, for the mixture by solving a relationship comprising:

$$\log T'_{2LM} = f_{OBMF} \cdot \log T_{2OBMF} + (1 - f_{OBMF}) \cdot \log T_O;$$

where
- $f_{OBMF}$ represents a fraction for oil based mud filtrate (OBMF);
- $T_{2OBMF}$ represents a relaxation time for the OBMF in a separate state; and
- $T_{2O}$ represents a relaxation time for oil in a separate state.

19. The computer program product as in claim 18, wherein the calculating comprises computing an OBMF fluid fraction, $f_{OBMF}$, for the mixture by solving a relationship comprising:

$$f_{OBMF} = \log \frac{T'_{2LM}}{T_{2O}} \bigg/ \log \frac{T_{2OBMF}}{T_{2O}};$$

where
- $T'_{2LM}$ represents the mean response transverse relaxation time;
- $f_{OBMF}$ represents a fraction for oil based mud filtrate (OBMF);
- $T_{2OBMF}$ represents a relaxation time for the OBMF in a separate state; and
- $T_{2O}$ represents a relaxation time for oil in a separate state.

20. The computer program product as in claim 19, wherein the calculating further comprises calculating an oil fraction from the OBMF fluid fraction.

* * * * *